United States Patent [19]

Fealy et al.

[11] Patent Number: 5,656,257

[45] Date of Patent: Aug. 12, 1997

[54] SHAMPOO AND CONDITIONING COMPOSITION

[75] Inventors: Barbara J. Fealy, Columbia Heights; Audrey I. Reinbold, Fridley, both of Minn.

[73] Assignee: Electronics Hair Styling, Inc., Fridley, Minn.

[21] Appl. No.: 430,624

[22] Filed: Apr. 28, 1995

[51] Int. Cl.$^6$ ............................ A61K 7/06; A61K 7/075
[52] U.S. Cl. ........................ 424/70.13; 424/70.11; 424/70.16; 424/70.17; 424/78.03
[58] Field of Search ................ 424/70.11, 70.12, 424/70.13, 70.16, 78.03

[56] References Cited

U.S. PATENT DOCUMENTS

| | | | |
|---|---|---|---|
| Re. 34,584 | 4/1994 | Grote et al. | 252/142 |
| 2,733,212 | 1/1956 | Epstein et al. | 252/117 |
| 4,529,773 | 7/1985 | Witiak et al. | 524/558 |
| 4,654,207 | 3/1987 | Preston | 424/70 |
| 4,704,272 | 11/1987 | Oh et al. | 424/70 |
| 4,983,383 | 1/1991 | Maksimoski et al. | 424/70 |
| 5,002,762 | 3/1991 | Bolich, Jr. | 424/70 |
| 5,030,374 | 7/1991 | Tranner | 252/90 |
| 5,034,218 | 7/1991 | Duvel | 424/70 |
| 5,057,241 | 10/1991 | Merritt | 252/174.17 |
| 5,059,414 | 10/1991 | Dallal et al. | 424/70 |
| 5,073,591 | 12/1991 | Tsauk | 524/460 |
| 5,078,990 | 1/1992 | Martin et al. | 424/70 |
| 5,085,857 | 2/1992 | Reid et al. | 424/70 |
| 5,114,706 | 5/1992 | Duvel | 424/70 |
| 5,221,530 | 6/1993 | Janchitraponvej et al. | 424/70 |
| 5,248,445 | 9/1993 | Rizvi et al. | 252/174.15 |
| 5,344,643 | 9/1994 | Thiel et al. | 424/70 |
| 5,358,667 | 10/1994 | Bergmann | 252/547 |
| 5,376,146 | 12/1994 | Casperson | 8/408 |
| 5,384,114 | 1/1995 | Dowell et al. | 424/70.1 |

OTHER PUBLICATIONS

Cosmetics & Toilietries, vol. 96, Jul. 1991 p. 66.
Aculyn personal care polymer, Rohm Haas 1990.
Cosmetics & Toiletries, vol. 103, Dec. 1988 specifications with Characteristics of Emery Chemicals, Technical bulleting 100F, Henkel Corporation.

*Primary Examiner*—Sallie M. Gardner
*Attorney, Agent, or Firm*—Moore & Hansen

[57] ABSTRACT

Disclosed is an anionic shampoo and conditioning composition comprising an oily conditioning agent, a shampooing agent, a acrylate copolymer, a cationic conditioning agent, and water. In another embodiment the composition further comprises a $C_8$ to $C_{18}$ fatty acid. The composition provides enhanced conditioning properties utilizing both oily and cationic conditioning agents in combination with an anionic acrylate copolymer while maintaining stability and dispersion.

5 Claims, No Drawings

SHAMPOO AND CONDITIONING COMPOSITION

The present invention relates to a stable shampoo composition providing enhanced conditioning, foaming and stability properties and a method of use therefor.

BACKGROUND

Hair care compositions which claim to impart both shampoo and conditioner properties to the hair at the same time are well known in the art. Such compositions typically contain one or more surfactants for shampooing or cleaning purposes, one or more "conditioning" agents for the purpose of making hair easier to comb when wet, and more controllable when dry, and a suspending agent to suspend a conditioning agent in the composition. Typically, these conditioning agents are either water-insoluble oils or cationic resinous materials or surfactants or a combination of both. In compositions containing both an oily conditioning agent and a cationic resinous conditioning agent, the suspending agent also functioned to prevent the cationic conditioning agent and the commonly used anionic shampooing agent from inactivating one another.

Prior art teaches stabilizing a non-volatile silicone in an anionic surfactant base using xanthan gum, long chain esters of ethylene glycol, long chain fatty acids ($C_{18}$ and higher) containing a $C_{22}$ fatty acid, carboxyvinyl polymers, carboxyvinyl polymers in combination with long chain fatty alcohols, and particle size.

However, the use of some suspending agents in combination with the above ingredients necessitated the used of in-line mixing of at least three separate suspensions or dispersions that had to be premixed in three separate tanks. In-line mixing added cost and complexity to the manufacture of high volume consumer hair care products. It would be desirable to have a more efficient production process.

Additionally, it would be desirable to have an easy to manufacture shampoo and conditioning composition providing both enhanced shampooing and conditioning without compromising shelf-stability. Further, desirably, the composition utilizes both oily conditioning agents and cationic conditioning agents to provide enhanced conditioning. Further, desirably, such oily conditioning agent will be suspendible and stabilizable with an anionic acrylate copolymer alone or in combination with a fatty acid, both ingredients commercially available at uniform activity levels. Further, desirably, the acrylate copolymer and the fatty acid will be compatible with and not inactivate the cationic conditioning agent or agents. Further desirably, such conditioning agents may be incorporated into an anionic shampoo system.

Heretofore, compositions utilizing cationic conditioning agents and other known suspending agents have been difficult to prepare due to the incompatibility of the two substances and the processing requirements of the particular suspending agent. Accordingly, it would be desirable to have shampoo and conditioning compositions wherein the processing time is substantially reduced and wherein the incompatibility problem is also circumvented.

It would be desirous to provide a suspension system for the suspension of a non-volatile silicone and a cationic resin to provide superior conditioning properties and which reduces the processing time of the composition. The present invention addresses the problem of suspending a non-volatile silicone in an anionic surfactant system in an economical manner.

SUMMARY OF THE INVENTION

It has been surprisingly discovered that the use of an acrylate copolymer alone or in combination with a fatty acid in an anionic shampoo and conditioning composition containing an anionic surfactant, a cationic conditioning agent and an oily conditioning agent, stably suspends the oily conditioning agent with consumer acceptable foaming and which can be made using a conventional tank and mixing equipment, resulting in a processing time savings of at least about 50% over a process requiring in-line mixing and three mixing vessels.

In its broadest form, the present invention is a shampoo and conditioning composition comprising an oily, substantially water-insoluble conditioning agent, a shampooing agent, an amount of an acrylate copolymer sufficient to suspend and stabilize the oily conditioning agent, a cationic conditioning agent, and water.

In another embodiment, the present invention is a shampoo and conditioning composition comprising an oily, substantially water-insoluble conditioning agent, a shampooing agent, an amount of an acrylate copolymer and of a fatty acid sufficient to suspend and stabilize the oily conditioning agent, a cationic conditioning agent, and water. The acrylate copolymer in the above embodiments comprises an emulsion copolymer obtained by aqueous emulsion copolymerization of (1) about 20 percent to about 50 percent by weight methacrylic acid or acrylic acid, (2) about 0.5 percent to about 25 percent by weight of an acrylic or methacrylic acid ester of a $C_8$–$C_{30}$ alkyl, alkylaryl, or polycyclic hydrocarbyl monoether of a polyethylene glycol having at least two oxyethylene units, this ester being defined by the following general formula:

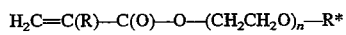

$$H_2C\!=\!C(R)\!-\!C(O)\!-\!O\!-\!(CH_2CH_2O)_n\!-\!R^*$$

where R is H or CH3, n is from 2 to about 60, and R* is a hydrophobic alkyl, alkylaryl, or polycyclic alkyl group having 8 to 30 carbon atoms, and (3) about 40 percent to about 60 percent by weight of a $C_1$–$C_4$ alkyl acrylate or methacrylate, the sum of the percentages of the copolymer components being equal to 100 percent.

Further according to the present invention, there is a method of shampooing and conditioning hair comprising applying the composition described above to wet hair and then rinsing the composition out of the hair.

Further according to the present invention, there is a shampoo and conditioning composition wherein the shampooing agent is an anionic surfactant, a cationic surfactant, or an amphoteric surfactant.

Further according to the present invention, there is a shampoo and conditioning composition wherein the cationic conditioning agent is a quaternary polysaccharide, a quaternary polysaccharide derivative, a quaternary polyamide, a cationic polyacrylate, a cationic polymethacrylate, a cationic polyacrylamide, a cationic polymethacrylamide, or butylene oxide/propylene oxide/ethylene oxide derivatives of tetraalkylammonium salts.

DETAILED DESCRIPTION OF THE INVENTION

The present invention fixes the oil in a matrix to stabilize product for a two year shelf-life. The oil particles are homogeneous. The resultant product is an easy to manufacture reducing processing time by at least 50% over an in-line mixing process. The shampoo compositions provide superior conditioning (ease of comb, softness, static control) to hair without the need of a separate post-shampoo conditioner. The present product does not interfere with the cleansing or foaming properties of the shampoo and does not leave a buildup on hair after repeated use.

Acrylate copolymers useful in the present invention comprise copolymers obtained by aqueous emulsion copolymerization of the three following monomers, and optionally a fourth monomer as set forth below:

1) Methacrylic acid or acrylic acid,

2) An acrylic or methacrylic acid ester of a $C_8$–$C_{30}$ alkyl, alkylaryl, or polycyclic hydrocarbyl monoether of a polyethylene glycol having at least two oxyethylene units, preferably having 10–40 oxyethylene units, this ester being defined by the following general formula:

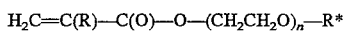

$$H_2C=C(R)-C(O)-O-(CH_2CH_2O)_n-R*$$

wherein R is H or $CH_3$, the latter being preferred, n is at least 2, and preferably has an average value of at least 10, up to 40 to 60 or even up to 70 or so, and R* is a hydrophobic group, for example an alkyl, alkylaryl, or polycyclic alkyl group having from 8 to 30 carbon atoms, preferably 16 to 18 carbon atoms, or having an average of 12 to 18 or more carbon atoms, 3) A $C_1$–$C_4$ alkyl acrylate or methacrylate, preferably ethyl acrylate, butyl acrylate, or methyl methacrylate, and 4) Optionally, a small amount of a polyethylenically unsaturated monomer.

In general, the emulsion copolymer dispersions obtained have a solids content from 25–50 percent by weight, and the 3 component copolymer dispersion has a weight average molecular weight of about 100,00 to several million.

The relative proportions of the first three components fall in the range of 1) 20–50 weight percent, 2) 0.5 to 25 weight percent, and 3) at least 30 weight percent, the total percentages of the three components being 100. In component 2), R* may be $C_8$, $C_{12}$, $C_{13}$, $C_{14}$, or $C_{15}$, preferably $C_{12}$ to $C_{18}$ or mixtures thereof, examples being lauryl, cetyl, palmityl, and stearyl. These emulsion copolymers may be produced by conventional aqueous emulsion polymerization techniques using appropriate emulsifiers for emulsifying the monomer and for maintaining the polymer obtained in a stable-dispersed condition. The acrylate copolymer must be at least partially neutralized with a suitable neutralizing agent before acidification of the composition with a suitable acid. The partially neutralized or neutralized acrylate copolymer must also be in the presence of a surfactant at the time acidification occurs.

A preferred acrylate copolymer has the Cosmetic, Toiletry, and Fragrance Association (CTFA) name of Acrylates/Steareth 20 Methacrylate Copolymer and has the trade name of ACULYN® 22 Polymer, available as a 30% solution from Rohm and Haas. The CTFA dictionary defines Acrylates/Steareth 20 Methacrylate Copolymer as a polymer of the ester of methacrylic acid and Steareth 20 and one or more monomers of acrylic acid, methacrylic acid or one of their simple esters.

The acrylate copolymer preferably comprises between about 0.15 to about 5, more preferably between about 0.5 and about 2.5, and most preferably about 0.8 to about 1.5 weight percent of the composition.

Excellent teachings directed to acrylate copolymers useful in the present composition as well as methods of making and using are seen in U.S. Pat. No. 4,529,773, which is incorporated herein by reference.

The acrylate copolymer may function as both a thickener for the composition and as a suspending agent for the oily conditioning agent. The acrylate copolymer in the ranges defined above, is present in an amount sufficient to suspend and stabilize the oily conditioning agent. The acrylate copolymer is partially or substantially neutralized or esterified sufficient to provide the desired level of suspending capacity or thickening if used as a thickener.

Suitable neutralizing agents for the acrylate copolymer include those known in the art as well as alkali anionic surfactants which provide the additional neutralizing effect. The neutralizing agent may be an organic or inorganic substance having a basic moiety capable of partially or substantially neutralizing the acrylate copolymer. Useful neutralizing agents include alkali and alkaline earth metal hydroxides; mono-, di-, and tri-aliphatic amines containing from about 1 to about 20 carbon atoms in the aliphatic carbon chain with the same or different substituent groups in the di- and tri-compounds; and alkanolamines containing from 1 to about 12 carbon atoms in the alkyl group. Suitable alkali metal hydroxides include those of sodium, potassium, and lithium. Suitable alkanolamines include mono-, di-, and tri-ethanolamines, ethanolamines, propanolamines, isopropanolamines, and the like. A preferred neutralizing agent is triethanolamine. The acrylate copolymer must be at least partially neutralized prior to acidification of the mixture and in the presence of the surfactant at the time acidification occurs.

The mixture may be acidified with any acid that is capable of reducing the pH to the desired level. Suitable acids include mono- and poly-carboxylic acids. The most preferred acid is citric acid.

Additionally, the composition may also contain one or more fatty acids which suspends the oily conditioning agent and opacifiers in the composition. Generally, any fatty acid or combinations of acids having from about 8 to 18 carbons atoms is suitable for use in the present invention. Some of the fatty acids useful in the present composition include commercially available caprylic (99%$C_8$, 1% $C_{10}$; 56% $C_8$, 40%$C_{10}$, 3% $C_6$), capric (97% $C_{10}$, 2% $C_{12}$, 1% $C_8$), lauric (96% $C_{12}$, 3% $C_{14}$, 1% $C_{10}$; 99% $C_{12}$), myristic (99% $C_{14}$; 97% $C_{14}$, 2% $C_{16}$), palmitic (91% $C_{16}$, 4.5% $C_{17}$, 4% $C_{18}$), and stearic (95% $C_{18}$, 5% $C_{16}$; 90% $C_{18}$, 7% $C_{16}$, 3% $C_{20}$; 83% $C_{18}$, 11% $C_{16}$, 2% $C_{17}$, 2% $C_{14}$ 1% $C_{15}$; 55% $C_{18}$, 41% $C_{16}$, 3% $C_{14}$, 1% $C_{17}$; 65% $C_{18}$, 29% $C_{16}$, 4% $C_{14}$, 1.5% $C_{17}$; 63% $C_{18}$, 25% $C_{16}$, 3% $C_{14}$, 2% $C_{17}$; 50% $C_{16}$, 45.5% $C_{18}$, 2.5% $C_{14}$, 1.5% $C_{17}$) acids, and other commercially available blends available, for example, under the trade names of EMERSOL® and EMERY® from Henkel. Preferably, the fatty acid is stearic acid and is commercially available as a blend of about 50 percent palmitic acid and 45.5 percent stearic acid. The amount of fatty acid used in compositions of the present invention can be varied by the amount of acrylate copolymer used, the type of fatty acid used, and the desired appearance of the formulation. The fatty acid may generally comprise from about 0.05 to about 5 percent by weight of the composition, preferably from about 0.1 to about 2.0 and more preferably from about 0.1 to about 0.8 weight percent.

One advantage of using a fatty acid in the present invention is that the fatty acid acts as a suspending agent which provides for the suspending of a greater amount of oily conditioning agent than with the acrylate copolymer alone. The addition of a fatty acid to the composition increases the amount of an oily conditioning agent that may be suspended and increases the stability of the composition having higher levels of an oily conditioning agent. Thus, a more economical product may be made by using a fatty acid in combination with a lesser quantity of acrylate copolymer to suspend the oily conditioning agent in the present composition.

When the present composition contains a fatty acid, the amount of acrylate copolymer may be maintained to suspend a greater amount of an oily conditioning agent. Or, the amount of the acrylate copolymer may be reduced to make a more economical product. Generally, the amount of acrylate copolymer used in the present composition containing a fatty acid is from about 0.15 to about 5 percent by weight of the composition and is preferably from about 0.6 to about 1.2 percent and most preferably about 0.8 to about 1.1 percent by weight of the composition.

Furthermore, the fatty acids used in the compositions of the present invention have an opacifying effect on the composition when combined with a suitable neutralizing agent to form a salt of the fatty acid. Neutralizing agents used to neutralize the acrylate copolymer are suitable to neutralize fatty acids. Other suitable neutralizers for the fatty acids include magnesium sulfate, metal hydroxides, and alkyl amines such as ethanolamine, triethanolamine, lauramide diethanolamine and stearamine or mixtures thereof. The opacifying effect of fatty acids gives the compositions of the present invention a more consumer acceptable appearance.

The present composition contains a cationic resin or surfactant as a cationic conditioning agent to enhance the present composition's conditioning performance. Preferably, the conditioning agent is a cationic resin or a cationic surfactant having a weight average molecular weight of about 400 or greater and more preferably about 1000 to about 3 million. Suitable cationic resins and surfactants used in the present composition include for example the following: cationic or quaternized polysaccharides or polysaccharide derivatives; cationic or quaternized polyamides; cationic or quaternized polymeric derivatives of acrylates, methacrylates, acrylamides, methacrylamides, or copolymers thereof; and tetraalkylammonium salts and BO/PO/EO (butylene oxide/propylene oxide/ethylene oxide) derivatives thereof.

Suitable cationic or quaternized polysaccharides or polysaccharide derivatives used in the present composition include, for example, those of cellulosic polymers, guar gums, xanthan gums, locust bean gums, gum arabic starches, starch amyloses, alginates, and the like. Excellent teachings directed to useful polysaccharides and polysaccharide derivatives are seen in The Encyclopedia of Polymer Science and Engineering, 2 ed., vol. 7, pp. 589 to 613, which is incorporated herein by reference.

Particularly useful cationic or quaternized polysaccharides or polysaccharide derivatives are those of the guar gums and guar gum derivatives. Guar gums include those of high molecular weight carbohydrates or polysaccharides made up of linked mannose and galactose units. The molecule may be a straight chain of mannose units linked to each other by means of beta (1–4) glycosidic linkages. Galactose units may branch from alternate mannose units through alpha (1–6) linkages with the mannose units. Useful guar gums include cationic or quaternized derivatives of hydroxypropyl, hydroxyethyl, sodium carboxymethyl, and carboxymethylhydroxypropyl guar gums. A most preferred cationic guar gum resin is 2-hydroxypropyltrimonium chloride. Teachings directed to guar gums are seen in U.S. Pat. Nos. 4,678,606 and 4,491,539, both of which are incorporated herein by reference.

Other useful cationic or quaternized polysaccharides or polysaccharide derivatives include those of the cellulosic polymers such as methyl, ethyl, hydroxypropyl, hydroxyethyl, carboxymethyl, and carboxymethylhydroxypropyl cellulose. A representative quaternized cellulosic polymer is trimethylammonium hydroxyethylcellulose such as Polymer JR (Union Carbide Corp.).

Other cationic resins useful as conditioning agents include cationic or quaternized polyamides. Examples of such resins include cocodimonium hydrolyzed animal keratins such as Croquat WKP and steartrimonium hydrolyzed animal keratins such as Croquat Q (Croda Inc.).

Other cationic resins useful as conditioning agents include cationic or quaternized polymeric derivatives of acrylates, methacrylates, acrylamides, methacrylamides or copolymers, thereof as described by the following:

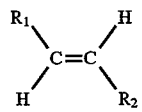

$R_1$=H, $CH_3$
$R_2$=H, Alkyl Radical, —$COOR_3$, —$COR_4$
$R_3$=$C_1$–$C_{20}$ Saturated, unsaturated, branched or cycled alkyl radical

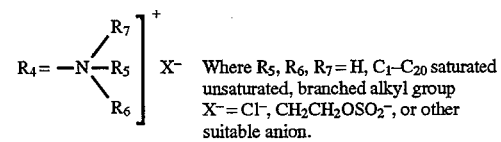

Where $R_5$, $R_6$, $R_7$ = H, $C_1$–$C_{20}$ saturated unsaturated, branched alkyl group
$X^-$ = $Cl^-$, $CH_2CH_2OSO_2^-$, or other suitable anion.

Examples of the above resins include dimethylaminoethylmethacrylate/vinyl pyrrolidone copolymers such as Gafquat 755 (GAF Corp.) and acrylamide/dimethyldiallylammonium chlorides such as Merquat 550 such as (Merck & Co.).

Other cationic resins useful as conditioning agents include cationic or quaternized polymeric derivatives of substituted allyl or vinyl compounds. Such compounds are of the general formula:

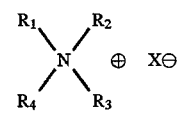

in which $R_1$ and $R_2$ are both vinyl radicals or both allyl radicals and $R_3$ and $R_4$ are the same or different and can be a lower alkyl or a fatty radical or represent a doubly bonded carbon of a cyclic residue containing $R_1$ or $R_2$ which may contain an additional heterocarbon; e.g. N, O or S. X is the counter ion, usually a halide such as bromide, chloride or iodide, and its identity is determined by the precursor raw materials known in the art. Said monomers can be copolymerized with either a monoethylenic compound such as ethylene, vinylbenzene, vinyl or allyl ester of acrylic or methacrylic acid or more preferably vinyl pyrrolidone such as Luviquat FC-370 (BASF). Representative resins copolymerized with cellulosic derivatives include the Celquat polymers (National Starch and Chemical).

Other cationic resins and surfactants useful as conditioning agents include tetraalkylammonium salts and BO/PO/EO (butylene oxide/propylene oxide/ethylene oxide) derivatives thereof.

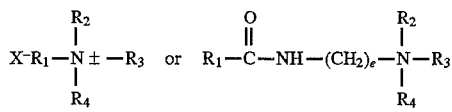

Where $X^- = Cl^-$, $CH_2CH_2OSO_2^-$, or other suitable anion
$R_1 = C_{12}-C_{24}$

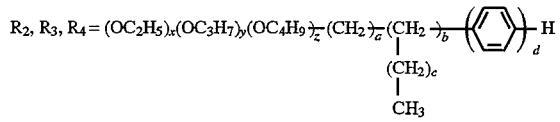

Where:
- a=0–24  e=2–3
- b=0–10  x=0–50
- c=0–5   y=0–25
- d=0–1   z=0–15

Generally the cationic conditioning agent is present in the composition from about 0.05 to about 5 weight percent of the composition, preferably from about 0.05 to about 1 weight percent and more preferably from about 0.05 to about 0.5 weight percent of the composition.

Suitable oily conditioning agents are oily, substantially water-insoluble substances which provide conditioning effects to the hair.

The present composition preferably contains a silicone material as the oily conditioning agent to deliver some measure of softness and wet-combing and to aid in processing of the composition. The silicone materials may comprise preferably from about 0.1 to about 10 and more preferably from about 0.5 to about 4 weight percent of the composition and even more preferably from about 0.5 to about 2.0 weight percent of the composition.

The silicone material may be soluble or insoluble in water. Suitable water-insoluble silicone materials include polyalkylsiloxanes, polyarylsiloxanes, polyalkylarylsiloxanes, polysiloxane gums, and polyethersiloxane copolymers. Water-insoluble silicone materials may be considered oily conditioning agents as described previously. Teachings directed to suitable water-soluble and insoluble silicone materials are found in U.S. Pat. Nos. 4,788,006; 4,341,799; 4,152,416; 3,964,500; 3,208,911; 4,364,837 and 4,465,619, all of which are incorporated herein by reference. Suitable water-soluble silicones include polyether/polysiloxane block copolymers as represented by the formula

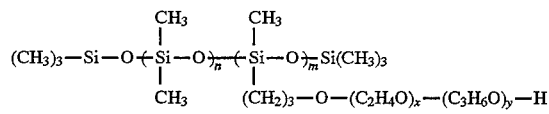

wherein n is from 10 to 80, m is from 0 to 50, x is from 20 to 100, y is from 0 to 80. Examples of additional silicone materials includes Dow Corning 200, 345, and 3225C and General Electric SF-1202, SF18 (350) and others. Preferred silicone materials used as an oily conditioning agent are polydimethylsiloxanes which have the CTFA designation of dimethicone and which range in viscosity from 5 to 100,000 centistokes (cs) at 25° C. A preferred dimethicone has a viscosity of about 60,000 cs and is available from Dow Corning. Additionally, the number average particle size of the silicone material after mixing is greater than 2 microns.

Other suitable oily conditioning agents include, but are not limited to the following: mineral oils and saturated or unsaturated vegetable oils such as soybean oil, babassu oil, castor oil, cottonseed oil, Chinese tallow oil, crambe oil, perilia oil, Danish rapeseed, rice bran oil, palm oil, palm kernel oil, olive oil, linseed oil, coconut oil, sunflower oil, safflower oil, peanut oil, and corn oil. The oily conditioning agent preferably comprises between about 0.1 to about 10, more preferably between about 0.5 to about 4 and most preferably about 0.5 to about 2.0 weight percent of the composition.

One of the important aspects of this invention is the stability of oily and cationic conditioning agents with the acrylate copolymer, the fatty acid and the surfactant, particularly preferred anionic surfactants, of the present composition. The term "stability" in the present composition means that the oily and cationic conditioning agent remain substantially homogeneously suspended and dispersed in the composition.

The present composition contains a shampooing agent comprising one or more surfactants, and functions to shampoo or clean the hair. The surfactants comprising the shampooing agent preferably comprise from about 5 to about 70, more preferably about 5 to about 20, and most preferably about 5 to about 12 active weight percent of the composition. Active weight percent refers to actual weight percent of the surfactant or surfactants in the composition, and not to the entire aqueous form in which the surfactant may be supplied for purposes of ease of formulation. The surfactant or surfactants may be anionic, nonionic, cationic, or amphoteric. Preferably, the surfactant or surfactants are anionic. For purposes of this specification, the anionic acrylate copolymers described above are not considered shampooing agent surfactants.

Cationic conditioning agents, whether cationic resins and cationic surfactants, are not considered shampooing agent surfactants in addition to being conditioning agents for purposes of this specification unless they have sufficient shampooing or cleaning efficacy to function as a shampooing agent standing alone in a typical commercial shampoo composition. Thus, a composition having a cationic resin or cationic surfactant functioning primarily as a conditioning agent rather than a shampooing agent may also have other lighter cationic surfactants, preferably those with a weight average molecular weight of less than about 400, which function primarily as shampooing agents.

Suitable anionic surfactants include alkyl and alkyl ether sulfates, or combinations thereof. These surfactants have the respective formula $ROSO_3M$ and $RO(C_2H_4O)_xSO_3M$ wherein R is an alkyl or alkenyl radical of preferably about 8 to about 22 and, more preferably about 10 to about 18 carbon atoms, x is 0 to 10 and M is a water-soluble cation such as ammonium, sodium, potassium, and triethanolamine. A preferred alkyl sulfate is R=12–14, and M=$NH_4$ cation (ammonium lauryl sulfate).

Other suitable anionic surfactants include alkyl and alkylbenzene sulfonates and succinates and sulfosuccinates having from about 8 to about 24 carbon atoms. Suitable derivatives include the ammonium, sodium, potassium, and triethanolamine salts thereof.

Many varieties of suitable anionic surfactants as well as other types of surfactants are disclosed in U.S. Pat. Nos. 3,723,357; 4,788,006; 4,364,837 and 4,491,539, all of which are incorporated herein by reference.

The present composition preferably has a pH from about 4 to about 10 and more preferably from about 4 to about 6.

Water is an essential component of the present composition, and comprises preferably from about 30 to about 90 and more preferably from about 40 to about 80 weight percent of the composition.

The compositions of the present invention may also contain a nonionic alkanolamide foam stabilizer in an of about 0.5 to about 5 percent by weight of the composition.

Suitable alkanolamides include those known in the art of hair care formulations such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleyamide DEA, tallowamide DEA, lauramide MIPA, tallowamide MEA, isostearamide DEA, isostearamide MEA, and combinations thereof.

The present composition may further include optional ingredients, for example, preservatives, pearlescing agents, antidandruff agents, pH adjusting agents, foam stabilizers, perfumes, colorants and other opacifiers.

The preferred process according to the present invention for making the present composition is a simple, one tank mixing process. First, water is added to the tank and the water is agitated at the maximum level. The cationic conditioning agent is added and is mixed until dispersed. Agitation is reduced and the acrylate suspending agent is added and mixed. The shampooing agent is added to the tank and heat is applied to the tank. During heating to about 155° F. (68° C.), the pH is adjusted to about 6 using an alkaline pH adjuster. When the solution is homogeneous, the solution is cooled to about 95° F. (35° C.). The oily conditioning agent is admixed at high agitation until homogeneous. Other optional ingredients are then added, the pH is adjusted to about 4.8 to about 5.3, and the batch is mixed for about 15 minutes.

When the composition contains fatty acid, the fatty acid or acids, and a neutralizer for the fatty acid is added during the heating step as above, and the mixture is heated to a maximum temperature of about 185° F. (85° C.).

In using the compositions of the present invention to wash and condition hair, the method of application comprises applying about 0.1 to about 10 grams of the present composition to wet hair and then rinsing the composition from the hair.

The invention may be more fully understood by reference to the following examples which illustrate, but by no means, limit the scope of the invention.

EXAMPLES

Examples 1–9

The following compositions in Table 1 are representative of one embodiment of the present invention. All amounts are weight percent unless otherwise indicated.

TABLE 1

| INGREDIENTS | Ex. 1 Wt. % | Ex. 2 Wt. % | Ex. 3 Wt. % | Ex. 4 Wt. % | Ex. 5 Wt. % | Ex. 6 Wt. % | Ex. 7 Wt. % | Ex. 8 Wt. % | Ex. 9 Wt. % |
|---|---|---|---|---|---|---|---|---|---|
| Water | QS | QS | QS | QS | QS | QS | QS | QS | QS |
| Guar Hydroxyl Propyl Trimonium Chloride | 0.10 | 0.10 | 0.10 | 0.10 | 0.30 | 0.30 | 0.30 | 0.30 | 0.30 |
| Acrylates/Steareth-20 Methacrylate Copolymer (ACULYN 22) (30% active) | 3.30 | 3.30 | 3.30 | 3.30 | 3.50 | 3,70 | 3.50 | 3.70 | 3.50 |
| Ammonium Lauryl Sulfate (28% active) | 37.0 | 37.0 | 37.0 | 37.0 | 37.0 | 37.0 | 37.0 | 37.0 | 37.0 |
| Triethanolamine | 0.25 | 0.25 | 0.25 | 0.25 | 0.25 | 0.25 | 0.25 | 0.25 | 0.25 |
| Ethylene Glycol Distearate | — | — | — | — | — | 0.40 | 0.40 | 0.40 | 0.40 |
| Stearic Acid (45.5% $C_{18}$, 50% $C_{16}$) | — | — | — | — | — | — | — | — | — |
| Palmitic Acid (91% $C_{16}$, 4.5% $C_{17}$, 4% $C_{18}$) | — | — | — | — | — | — | — | — | — |
| Palmitic Acid | — | — | — | — | — | — | — | — | — |
| Wheat Germ Oil[9] | — | — | — | — | — | — | — | — | — |
| Dimethicone Copolyol | — | — | — | — | — | — | — | — | — |
| Dimethicone Polymer BAF-589* | 1.00 | 0.75 | 1.00 | 1.00 | 1.00 | 1.00 | 1.00 | 1.00 | 1.00 |
| Lauramide diethanolamine | 3.50 | 3.50 | 3.50 | 3.50 | 3.00 | 3.00 | 3.00 | 3.00 | 3.00 |
| Methylchloroisothiasolinone, Methylisothiazolinone | 0.03 | 0.03 | 0.03 | 0.03 | 0.03 | 0.03 | 0.03 | 0.03 | 0.03 |
| Fragrance | 0.65 | 0.65 | 0.65 | 0.65 | 0.65 | 0.65 | 0.65 | 0.65 | 0.65 |
| Citric Acid | 0.42 | 0.42 | 0.42 | 0.42 | 0.42 | 0.42 | 0.42 | 0.42 | 0.42 |
| Ethylene Glycol Mono Stearate | 1.00 | 1.00 | 0.40 | — | 0.40 | — | — | | |
| Styrene/Acrylamide Copolymer, Ammonium Nonoxynol-4 Sulfat (Lytron 308) | — | — | — | — | — | — | — | 0.40 | 0.40 |

*Experimental Aqueous Dispersion (Rohm & Haas)

Examples 10–30

The following compositions contain fatty acid and are representative of another embodiment of the present invention.

TABLE 2

| INGREDIENTS | Ex. 10 Wt. % | Ex. 11 Wt. % | Ex. 12 Wt. % | Ex. 13 Wt. % | Ex. 14 Wt. % | Ex. 15 Wt. % |
|---|---|---|---|---|---|---|
| Water | QS | QS | QS | QS | QS | QS |
| Guar Hydroxy Propyl Trimonium Chloride | 0.10 | 0.10 | 0.30 | 0.30 | 0.30 | 0.30 |
| Acrylatels Steareth-20 Methacrylate Copolymer (ACULYN 22) (30% active) | 3.30 | 3.30 | 4.00 | 4.00 | 4.00 | 4.00 |

TABLE 2-continued

| Ingredient | | | | | | |
|---|---|---|---|---|---|---|
| Ammonium Lauryl Sulfate (28% active) | 37.0 | 37.0 | 40.00 | 40.00 | 40.00 | 40.00 |
| Triethanolamine | 0.25 | 0.25 | 0.25 | 0.25 | 0.25 | 0.25 |
| Ethylene Glycol Distearate | 0.20 | 0.10 | 0.20 | 0.20 | 0.20 | 0.20 |
| Stearamine | 0.50 | 0.50 | 0.50 | 0.50 | 0.50 | 0.50 |
| Stearic Acid (45.5% $C_{18}$, 50% $C_{16}$) | 0.50 | 0.50 | 0.50 | 0.50 | 0.50 | 0.50 |
| Palmitic Acid (91% $C_{16}$, 4.5% $C_{17}$, 4% $C_{18}$) | — | — | — | — | — | — |
| Palmitic Acid (74.5 $C_{16}$, 23 $C_{18}$, 1.5% $C_{14}$) | — | — | — | — | — | — |
| Wheat Germ Oil | — | — | — | — | — | — |
| Dimethicone Copolyol | — | — | — | — | — | — |
| Dimethicone | 1.00 | 1.00 | — | — | — | 4.00 |
| Polymer BAF-589* | — | 0.10 | — | — | — | — |
| Amodimethicone, Tallow trimonium chloride, Nonoxynol 10 (Dow Corning 929 Emulsion) | — | — | 2.00 | 4.00 | — | — |
| Trimethylsilylamodimethicone | — | — | — | — | 1.00 | — |
| Lauiamide diethanolamine | 3.50 | 3.50 | 3.50 | 3.50 | 3.50 | 3.50 |
| Methylchloroisothiasolinone, Methylisothiazolinone | — | — | — | — | 1.00 | — |
| Fragrance | 0.50 | 0.40 | — | — | — | — |
| Citric Acid | 0.45 | 0.45 | 0.45 | 0.45 | 0.45 | 0.45 |

| INGREDIENTS | Ex. 16 Wt. % | Ex. 17 Wt. % | Ex. 18 Wt. % | Ex. 19 Wt. % | Ex. 20 Wt. % | Ex. 21 Wt. % |
|---|---|---|---|---|---|---|
| Water | QS | QS | QS | QS | QS | QS |
| Guar Hydroxy Propyl Trimonium Chloride | 0.30 | 0.11 | 0.30 | 0.30 | 0.10 | 0.30 |
| Acrylates/Steareth-20 Methacrylate Copolymer (ACULYN 22) (30% active) | 4.00 | 3.63 | 3.70 | 3.70 | 3.30 | 3.00 |
| Ammonium Lauryl Sulfate (28% active) | 40.0 | 28.70 | 37.0 | 37.0 | 37.0 | 37.00 |
| Triethanolamine | 0.25 | 0.275 | 0.25 | 0.25 | 0.25 | 0.25 |
| Ethylene Glycol Distearate | 0.20 | — | 0.30 | 0.30 | 0.10 | — |
| Stearamine | 0.50 | — | 0.50 | 0.49 | 0.50 | 0.10 |
| Stearic Acid (45.5% $C_{18}$, 50% $C_{16}$) | 0.50 | 2.00 | 0.25 | 0.255 | — | — |
| Palmitic Acid (91% $C_{16}$, 4.5% $C_{17}$, 4% $C_{18}$) | — | — | 0.25 | 0.255 | 0.50 | — |
| Palmitic Acid (74.5% $C_{16}$, 23% $C_{18}$, 1.5% $C_{14}$) | — | — | — | — | — | 0.10 |
| Wheat Germ Oil | — | — | — | — | — | — |
| Dimethicone Copolyol | — | — | — | — | — | — |
| Dimethicone | — | 1.10 | 3.00 | 1.00 | 1.00 | 1.00 |
| Polymer BAF-589* | — | — | — | — | 0.10 | 0.10 |
| Amodimethicone, tallow trimonium chloride, Nonoxynol 10 (Dow Corning 929 Emulsion) | — | — | — | — | — | — |
| Trimethylsilylamodimethicone | — | — | — | — | 0.10 | — |
| Lauriamide diethanolamine | 3.50 | 4.31 | 3.50 | 3.50 | 3.50 | 3.00 |
| Methylchloroisothiasolinone, Methylisothiazolinone | — | — | — | — | 1.00 | 0.03 |
| Fragrance | — | 0.715 | 0.80 | 0.80 | 0.40 | 0.65 |
| Citric Acid | 0.45 | 0.44 | 0.42 | 0.42 | 0.45 | 0.42 |
| $MgSO_4$ | — | 6.00 | — | — | — | — |

| INGREDIENTS | Ex. 22 Wt. % | Ex. 23 Wt. % | Ex. 24 Wt. % | Ex. 25 Wt. % | Ex. 26 Wt. % |
|---|---|---|---|---|---|
| Water | QS | QS | QS | QS | QS |
| Guar Hydroxy Propyl Trimonium Chloride | 0.30 | 0.30 | 0.30 | 0.30 | 0.30 |
| Acrylatels Steareth-20 Methacrylate Copolymer (ACULYN 22) (30% active) | 3.00 | 3.00 | 3.00 | 3.00 | 3.00 |
| Ammonium Lauryl Sulfate (28% active) | 37.0 | 37.00 | 37.0 | 37.00 | 37.00 |
| Triethanolamine | 0.25 | 0.25 | 0.25 | 0.25 | 0.25 |
| Ethylene Glycol Distearate | — | — | — | — | — |
| Stearamine | 0.30 | 0.50 | 0.50 | 0.50 | 0.50 |
| Stearic Acid (45.5% $C_{18}$, 50% $C_{16}$) | — | 0.30 | 0.40 | 0.50 | 0.50 |
| Palmitic Acid (91% $C_{16}$, 4.5% $C_{17}$, 4% $C_{18}$) | — | — | — | — | — |
| Palmitic Acid (74.5% $C_{16}$, 23% $C_{18}$, 1.5% $C_{14}$) | 0.30 | 0.30 | 0.40 | 0.50 | 0.50 |
| Wheat Germ Oil | — | — | — | — | — |
| Dimethicone Copolyol | — | — | — | — | — |
| Dimethicone | 1.00 | 1.00 | 1.00 | 2.00 | 1.00 |
| Polymer BAF-589* | 0.10 | 0.10 | 0.10 | 0.10 | 0.10 |
| Amodimethicone, tallow trimonium chloride, Nonoxynol 10 (Dow Corning 929 Emulsion) | — | — | — | — | — |
| Trimethylsilylamodimethicone | — | — | — | — | 0.10 |
| Lauriamide diethanolamine | 3.00 | 3.00 | 3.00 | 3.00 | 3.00 |
| Methylchloroisothiasolinone, Methylisothiazolinone | 0.03 | 0.03 | 0.03 | 0.03 | 0.03 |
| Fragrance | 0.65 | 0.65 | 0.65 | 0.65 | 0.65 |
| Citric Acid | 0.42 | 0.42 | 0.42 | 0.42 | 0.42 |

TABLE 2-continued

| INGREDIENTS | Example 27 Weight % | Example 28 Weight % | Example 29 Weight % | Example 30 Weight % |
|---|---|---|---|---|
| MgSO$_4$ | — | — | — | — |
| Water | QS | QS | QS | QS |
| Guar Hydroxyl Propyl Trimonium Chloride | 0.30 | 0.30 | 0.10 | 0.10 |
| Acrylates/Steareth-20 Methacrylate Copolymer (ACULYN 22) (30% active) | 3.00 | 3.70 | 3.30 | 3.30 |
| Ammonium Lauryl Sulfate (28% active) | 37.00 | 37.0 | 37.0 | 37.0 |
| Triethanolamine | 0.25 | 0.25 | 0.25 | 0.25 |
| Ethylene Glycol Distearate | — | 0.30 | 0.10 | 0.10 |
| Stearamine | 0.50 | 0.49 | 0.50 | 0.50 |
| Stearic Acid (45.5% C$_{18}$, 50% C$_{16}$) | 0.60 | — | — | — |
| Palmitic Acid (91% C$_{16}$, 4.5% C$_{17}$, 4% C$_{18}$) | — | — | — | — |
| Palmitic Acid (74.5% C$_{16}$, 23% C$_{18}$, 1.5% C$_{14}$) | 0.60 | 0.50 | 0.50 | 0.50 |
| Wheat Germ Oil | — | — | — | 2.00 |
| Dimethicone Copolyol | — | — | 2.00 | — |
| Dimethicone | 1.00 | 1.00 | — | — |
| Polymer BAF-589* | 0.10 | — | 0.10 | 0.10 |
| Amodimethicone, tallow trimonium chloride, Nonoxynol 10 (Dow Corning 929 Emulsion) | — | — | | |
| Trimethylsilylamodimethicone | 0.10 | — | | |
| Lauramide diethanolamine | 3.00 | 3.50 | 3.50 | 3.50 |
| Methylchloroisothiasolinone, Methylisothiazolinone | 0.03 | 0.03 | 0.03 | 0.03 |
| Fragrance | 0.65 | 0.80 | 0.65 | 0.65 |
| Citric Acid | 0.42 | 0.42 | 0.45 | 0.45 |
| MgSO$_4$ | — | — | — | — |

*Experimental Aqueous Dispersion (Rohm & Haas)

All of the Examples found in Tables 1 and 2 were prepared using the process described hereinbefore. All of the Examples were found to be stable for at least 2 weeks at 45° C. The results of testing Examples 1 and 10 showed good conditioning of hair and good overall performance.

Many modifications and variations of the invention as set forth above can be made without departing from the spirit and scope thereof and therefore only such limitations should be imposed as are indicated by the appended claims.

What is claimed is:

1. A shampoo and conditioning composition, comprising:

A) about 0.1 to about 10.0 weight percent of an oily, substantially water-insoluble conditioning agent;

B) about 5 to about 70 weight percent of a shampooing agent;

C) about 0.15 to about 5 weight percent of an acrylate copolymer comprising an emulsion copolymer obtained by aqueous emulsion copolymerization of (1) about 20 percent to about 50 percent by weight methacrylic acid or acrylic acid, (2) about 0.5 percent to about 25 percent by weight of an acrylic or methacrylic acid ester of a C$_8$–C$_{30}$ alkyl, alkylaryl, or polycyclic hydrocarbyl monoether of a polyethylene glycol having at least two oxyethylene units, this ester being defined by the following general formula:

$$H_2C=C(R)-C(O)-O-(CH_2CH_2O)_n-R*$$

wherein

R is H or CH$_3$, n is from 2 to about 60, and

R* is a hydrophobic alkyl, alkylaryl, or polycyclic alkyl group having 8 to 30 carbon atoms, and (3) about 40 percent to about 60 percent by weight of a C$_1$–C$_4$ alkyl acrylate or methacrylate, the sum of the percentages of the copolymer components being equal to 100 percent;

D) about 0.05 to about 5 weight percent of a cationic conditioning agent wherein the cationic conditioning agent is a quaternary polysaccharide, a quaternary polyamide, a cationic polyacrylate, a cationic polymethacrylate, a cationic polyacrylamide a cationic polymethacrylamide, or butylene oxide/propylene oxide/ethylene oxide derivatives of tetraalkylammonium salts;

E) about 0.05 to about 5 weight percent of a C$_8$ to C$_{18}$ fatty acid or mixtures thereof; and F) about 30 to about 90 weight percent of water, wherein the amount of the acrylate copolymer and C$_8$ to C$_{18}$ fatty acid is sufficient to suspend the cationic conditioning agent, the oily conditioning agent and water within the composition.

2. The composition of claim 1 wherein the fatty acid is myristic, palmitic, stearic or mixtures thereof.

3. The composition of claim 1 wherein the fatty acid comprises a fatty acid containing about 50 percent of a C$_{16}$ fatty acid and about 45.5 percent of a C$_{18}$ fatty acid.

4. The composition of claim 1 wherein the fatty acid is a fatty acid containing about 91 percent of a C$_{16}$ fatty acid, about 4.5 percent of a C$_{17}$ fatty acid, and about 4 percent of a C$_{18}$ fatty acid.

5. A method of shampooing and conditioning hair, comprising: applying the composition of claim 1 to wet hair and then rinsing the composition out of the hair.

* * * * *